(12) United States Patent
Ramachandran et al.

(10) Patent No.: US 11,344,278 B2
(45) Date of Patent: May 31, 2022

(54) OVARIAN FOLLICLE COUNT AND SIZE DETERMINATION USING TRANSVAGINAL ULTRASOUND SCANS

(71) Applicant: KONINKLIJKE PHILIPS N.V., Eindhoven (NL)

(72) Inventors: Ganesan Ramachandran, Bangalore (IN); Sindhu Priyadarshini Nellur Prakash, Bangalore (IN); Celine Firtion, Bangalore (IN); Cecile Dufour, Paris (FR); Stéphane Allaire, Nanterre (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 189 days.

(21) Appl. No.: 16/485,294

(22) PCT Filed: Feb. 12, 2018

(86) PCT No.: PCT/EP2018/053375
§ 371 (c)(1),
(2) Date: Aug. 12, 2019

(87) PCT Pub. No.: WO2018/149765
PCT Pub. Date: Aug. 23, 2018

(65) Prior Publication Data
US 2019/0374193 A1 Dec. 12, 2019

(30) Foreign Application Priority Data
Feb. 20, 2017 (EP) .................................... 17305188

(51) Int. Cl.
*A61B 8/08* (2006.01)
*A61B 8/12* (2006.01)
*A61B 8/14* (2006.01)

(52) U.S. Cl.
CPC ............ *A61B 8/085* (2013.01); *A61B 8/0858* (2013.01); *A61B 8/12* (2013.01); *A61B 8/483* (2013.01); *A61B 8/145* (2013.01); *A61B 8/5207* (2013.01)

(58) Field of Classification Search
USPC ........................................................ 600/443
See application file for complete search history.

(56) References Cited

U.S. PATENT DOCUMENTS 5,997,479 A 12/1999 Savord et al.
6,013,032 A 1/2000 Savord
(Continued)

FOREIGN PATENT DOCUMENTS

IN 6266CH2014 GE 12/2014

OTHER PUBLICATIONS

Pierson, R. A., Olatunbosun, O. A., & Chizen, D. R. (1995). Ultrasonography and ovulation induction. Journal SOGC, 17(8), 739-750. (Year: 1995).*
(Continued)

*Primary Examiner* — Serkan Akar
*Assistant Examiner* — Renee C Langhals

(57) ABSTRACT

Disclosed is a computer-implemented method for determining an ovarian follicle count and size (diameter) from a pair of 2-D transvaginal ultrasound scans. The method comprises receiving the pair of 2-D (two-dimensional) transvaginal ultrasound scans, each scan comprising a plurality of 2-D ultrasound images captured along a translation direction of an ultrasound probe used to capture said scan, the respective translation directions being at least approximately orthogonal, and for each of said scans, the method further comprising detecting candidate follicles in the plurality of 2-D ultrasound images of the at least one 2-D transvaginal ultrasound scan; and segmenting the detected candidate
(Continued)

follicles to determine an average diameter for each candidate follicle; selecting the 2-D transvaginal ultrasound scan including the candidate follicle having the largest average diameter; and presenting the determined average diameters and the segmentations of the detected candidate follicles of the selected 2-D transvaginal ultrasound scan. A computer program product, ultrasound image processing device and ultrasound imaging system adapted to implement this method are also disclosed.

11 Claims, 10 Drawing Sheets

(56) References Cited

U.S. PATENT DOCUMENTS

| | | | |
|---|---|---|---|
| 6,283,919 | B1 | 9/2001 | Roundhill et al. |
| 6,328,693 | B1* | 12/2001 | Miyatake .................. A61B 8/14 600/437 |
| 6,458,083 | B1 | 10/2002 | Jago et al. |
| 6,623,432 | B2 | 9/2003 | Powers et al. |
| 2016/0292848 | A1* | 10/2016 | Plakas ..................... G16H 50/30 |
| 2017/0119355 | A1* | 5/2017 | Pintoffl ............... G01S 7/52063 |

OTHER PUBLICATIONS

Mashiach, R., Melamed, N., Gilad, N., Ben-Shitrit, G., & Meizner, I. (2011). Sonographic diagnosis of ovarian torsion: accuracy and predictive factors. Journal of Ultrasound in Medicine, 30(9), 1205-1210. (Year: 2011).*

Raine-Fenning, N., Jayaprakasan, K., Deb, S., Clewes, J., Joergner, I., Bonaki, S. D., & Johnson, I. (2009). Automated follicle tracking improves measurement reliability in patients undergoing ovarian stimulation. Reproductive biomedicine online, 18(5), 658-663. (Year: 2009).*

Gooding, M.J., "Volume Segmentation and Reconstruction from Freehand Three-Dimensional Ultrasound Data with Application to Ovarian Follicle Measurement". Ultrasound in Med. & Biol. vol. 34, No. 2, pp. 183-195, 2007.

Potocnik, B. et al., "Computerized detection and recognition of follicles in ovarian ultrasound images: a review", Medical & Biological Engineering & Computing, Springer, Berlin, DE, vol. 50, No. 12, Sep. 26, 2012, pp. 1201-1212.

Krivanek, A. et al., "Ovarian Ultrasound Image Analysis: Follicle Segmentation", IEEE Transactions on Medical Imaging, IEEE Service Center, NJ, vol. 17, No. 6, Dec. 1, 1998.

Prevention and management of infertility in primary healthcare settings, and information booklet for policy planners, program managers and service providers in healthcare systems, UNFPA, New Delhi, India (http://india.unfpa.org/drive/fertility.pdf).

Unisa, S. "Trends of infertility and childlessness in India: findings from NFHS data." Obgyn, 2010, 2 (2): 131-138. http://www.fvvo.belassets/91/09-Ganguly_et_al.pdf.

The Rotterdam ESHRE/ASRM-sponsored PCOS consensus workshop group. "Revised 2003 conensus on diagnostic criteria and long-term health risks related to polycystic ovary syndrome (PCOS)". Human Reproduction vol. 19, No. 1, pp. 41-47, 2004.

Dewailly, D. et al., "Diagnosis of polycystic ovary syndrome (PCOS): revisiting the threshold values of follicle count on ultrasound and of the serum AMH level for the definition of polycystic ovaries". Human Reproduction, vol. 26, No. 11, pp. 3123-3129, 2011.

Penzias, A.S. et al., "Ultrasound prediction of follicle volume: is the mean diameter reflective?" Fertility and Sterility, vol. 62, No. 6, Dec. 1994.

Deb, S. et al., "Intraobserver and interobserver reliability of automated antral follicle counts made using three-dimensional ultrasound and SonoAVC". Ultrasound Obstet Gynecol. Apr. 2009;33(4):477-83.

Jayaprakasan, K. et al., "3D ultrasound improves the interobserver reliability of AFC and facilitates increased clinical workflow". Ultrasound Obstet Gynecol. 2008; 31:439-444.

Ata, B. et al., "Comparison of automated and manual follicle monitoring in an unrestricted population of 100 women undergoing controlled ovarian stimulation for IVF". Human reprod 2011;26 (1) 127-133.

Raine-Fenning, N. et al. "Automated follicle tracking improves measurement reliability in patients undergoing ovarian stimulation". Reproductive biomedicine online 2009; 18 (5), 658-663.

Raine-Fenning et al., "Automated measurements of follicle diameter: a chance to standardize?" Fertil Steril 2009;91:1469-72.

Forman, R.G. et al., What is the true follicular diameter: an assessment of the reproducibility of transvaginal ultrasound monitoring in stimulated cycles; Fertility and Sterility, vol. 56, No. 5, Nov. 1991.

Stiros, S. et al., "Mean deformation tensor and mean deformation ellipse of an excavated tunnel section". International Journal of Rock Mechanics and Mining Sciences vol. 46, Issue 8, Dec. 2009, pp. 1306-1314.

International Search Report—PCT/EP2018/053375 dated Feb. 12, 2018.

Gooding, M. PhD Thesis. "3D Ultrasound Image Analysis in Assisted Reproduction". Merton College, University of Oxford, 2004.

Vanderkerckhove, F. et al., "The Value of Automated Follicle Volume Measurements in IVF/ICSI". Frontiers in Surgery, May 2014. vol. 1, article 18, pp. 1-12.

Shmorgun, et al., "Prospective cohort study of three-versus two-dimensional ultrasound for prediction of oocyte maturity", Fertility and Sterility, vol. 93, No. 4, pp. 1333-1337.

* cited by examiner

US 11,344,278 B2

OVARIAN FOLLICLE COUNT AND SIZE DETERMINATION USING TRANSVAGINAL ULTRASOUND SCANS

RELATED APPLICATIONS

This application is the U.S. National Phase application under 35 U.S.C. § 371 of International Application No. PCT/EP2018/053375, filed on Feb. 12, 2018, which claims the benefit of European Application No. 17305188.9, filed Feb. 20, 2017. These applications are hereby incorporated by reference herein.

FIELD OF THE INVENTION

The present invention relates to a computer-implemented method for determining ovarian follicle count and size from a 2-D transvaginal ultrasound scan.

The present invention further relates to a computer program product for implementing such a method.

The present invention further relates to an ultrasound image processing device for determining ovarian follicle count and size from a 2-D transvaginal ultrasound scan.

The present invention further relates to an ultrasound imaging system comprising such an ultrasound image processing device.

BACKGROUND OF THE INVENTION

Infertility is a worldwide problem, which is estimated to affect 8-12% of couples at some point in their lives. Infertility may have several causes. For example, female infertility can be caused by polycystic ovarian syndrome (PCOS), decreased ovarian reserve, tubal factors, hypothyroidism, and so on. Ultrasound (US) imaging is extensively used for diagnosis and monitoring of infertility in women, as the ovarian antral follicle count, i.e. the count of follicles having a diameter in a range of about 2-10 mm, which is an important indicator of female fertility, can be derived from such ultrasound images. For example, as is well known per se, antral follicles are associated with the storage of immature eggs in the ovary, such that the antral follicle count is considered a reliable indicator of the egg reserve in the ovary, optionally in combination with the determination of ovarian size and/or volume, for example using a well-known prolate ellipsoid formula. A high antral follicle count on the other hand may be indicative of PCOS, e.g. when observed in combination with an enlarged ovary.

Transvaginal US scanning is most commonly used to obtain meaningful (accurate) ultrasound images for ovarian evaluation, e.g. to diagnose infertility and monitor fertility treatment in women, e.g. by monitoring the number of follicles with a largest diameter in a range of 7-25 mm. Ideally, such transvaginal ultrasound imaging would involve the acquisition of 3-D (3-dimensional) ultrasound images of the ovaries of the female patient, as this facilitates a straight-forward evaluation of the follicle count and size within each ovary. An example of such a 3-D solution is disclosed in Indian patent application IN 2014/0626614 (application number 6266/CHE/2014) as published on 1 Jul. 2016, as well as in M. J. Gooding et al. In Ultrasound in Med. & Biol. Vol. 34, No. 2, pp 183-195, 2008 disclose a semi-automatic method for segmentation and reconstruction of freehand 3-D ultrasound data. Such 3-D ultrasound imaging has the advantage over 2-D (2-dimensional) ultrasound imaging that a sequence of 2-D images may be acquired with a stationary transvaginal ultrasound probe compared to the 2-D technique in which the clinician such as a sonographer or an infertility specialist such as a sonologist has to physically move the probe in a chosen direction, typically a direction in which the clinician expects to capture an optimal view of the follicles of interest. This is a trial and error approach, which is associated with a high probability that the clinician counted the same follicle multiple times, as well as missed some follicles, thereby increasing the risk of an inaccurate assessment of the follicle count and size within the ovaries of the female patient.

However, a drawback of 3-D ultrasound imaging systems is that such systems are significantly more costly than 2-D ultrasound imaging systems, such that market penetration of 3-D ultrasound imaging systems still is rather low, in particular in developing regions of the world. Therefore, there is a need to improve the reliability of 2-D ultrasound imaging in facilitating ovarian follicle evaluation by a clinician, for example to decrease inter-observer error and increase patient throughput.

US 2016/0292848 A1 discloses a medical imaging data processing apparatus comprises a setting circuitry configured to set a plurality of seeds at different locations in medical image data, a processing circuitry configured to select at least one seed from among the plurality of seeds and expand the at least one selected seed, and a region identifying circuitry configured to identify at least one target region based on a result of the expansion.

SUMMARY OF THE INVENTION

The present invention seeks to provide a computer-implemented method for determining ovarian follicle count and size from a 2-D transvaginal ultrasound scan that facilitates a more reliable evaluation of the ovarian follicles.

The present invention further seeks to provide a computer program product for implementing such a method.

The present invention further seeks to provide an ultrasound image processing device for determining an ovarian follicle count and size from a 2-D transvaginal ultrasound scan that facilitates a more reliable evaluation of the ovarian follicles.

The present invention further seeks to provide an ultrasound imaging system comprising such an ultrasound image processing device.

According to an aspect, there is provided a computer-implemented method for determining ovarian follicle count and size, comprising receiving a pair of 2-D (two-dimensional) transvaginal ultrasound scans, each scan comprising a plurality of 2-D ultrasound images captured along a translation direction of an ultrasound probe used to capture said scan, the respective translation directions being at least approximately orthogonal, and for each of said scans, the method further comprising detecting candidate follicles in the plurality of 2-D ultrasound images of the at least one 2-D transvaginal ultrasound scan; and segmenting the detected candidate follicles to determine an average diameter for each candidate follicle; selecting the 2-D transvaginal ultrasound scan including the candidate follicle having the largest average diameter; and presenting the determined average diameters and the segmentations of the detected candidate follicles of the selected 2-D transvaginal ultrasound scan.

The method of the present invention provides an automated manner in which a computer, typically an ultrasound image processing device, generates an overview of the average diameters of the follicles detected in an ultrasound scan of the vaginal region of the female patient from which the ovaries of that patient can be investigated. This method significantly reduces the risk of double-counted or missed follicles in the scan captured by the clinician, thereby resulting in reduced inter-observer variability as well as reduced scan time because the systematic scanning approach avoids the need for an ad-hoc scan in which the ultrasound probe is directed in response to observed features in the already captured ultrasound images on a trial and error basis, which is typically more time-consuming and therefore more uncomfortable for the patient. In addition, the likelihood of identifying the correct average diameter of the follicles including the largest follicle in the ovary or ovaries under investigation due to the evaluation of two sets of scans, which scans should be (sequentially) captured by the clinician in more or less (approximately) orthogonal directions relative to each other, preferably including a vertical or anterior to posterior (AP) scan and a horizontal or lateral to medial (LM) scan. This assists the method in determining the follicle diameters irrespective of their orientation in sight of the ovary, as the dimension or size of a follicle, which may have an elongated ellipsoid shape, will be accurately captured in one of the orthogonal scans. This results in reduced inter-observer variability as well as reduced scan time because the systematic scanning approach avoids the need for an ad-hoc scan in which the ultrasound probe is directed in response to observed features in the already captured ultrasound images on a trial and error basis, which is typically more time-consuming and therefore more uncomfortable for the patient.

In an embodiment, detecting candidate follicles in the plurality of 2-D ultrasound images comprises approximating a volume image from the plurality of 2-D ultrasound images; detecting an ovary in the approximated volume image; and detecting candidate follicles within the detected ovary. This is a particularly robust approach for detecting such candidate follicles, thereby reducing the risk of candidate follicles being overlooked.

Detecting candidate follicles within the detected ovary may further comprise determining a volume for each candidate follicle; and rejecting the candidate follicles that have a determined volume below a defined volume threshold for said subsequent segmenting. In this manner, false positives may be prevented from being needlessly segmented, thereby improving the efficiency of the method.

Preferably, the method further comprises creating a list of detected candidate follicles based on their determined average diameters for each of said scans, wherein said selecting the 2-D transvaginal ultrasound scan including the candidate follicle having the largest average diameter is based on said lists; and said presenting the determined average diameters and the segmentations of the detected candidate follicles in the selected 2-D transvaginal ultrasound scan comprises presenting the list of detected candidate follicles of the selected 2-D transvaginal ultrasound scan. Such a list, which preferably is an ordered list in which the candidate follicles are listed by decreasing or increasing average diameter, further facilitates the evaluation of the ultrasound scan data, for example to determine the follicle count and size as a measure of intermediate diagnostic relevance, which follicle characteristics for example may be used by a clinician to monitor the effectiveness of a fertility treatment of the female patient.

In an embodiment, detecting candidate follicles further comprises labelling the detected candidate follicles for further processing, to further aid the efficiency of the method.

To increase the accuracy of the evaluation of the ultrasound scans, the detecting possible follicles within the detected ovary may further comprise determining a characteristic for each candidate follicle selected from at least follicle volume, integrated intensity and maximum intensity; and rejecting the candidate follicles that have a determined characteristic outside an accepted range for said subsequent segmenting. This is based on the insight that any ovarian ultrasound scan typically comprises a number of false alarms, i.e. false positives, due to image regions being incorrectly recognized as candidate follicles. As such false positives are typically smaller or bigger than actual follicles, e.g. fall outside a range of 7-25 mm as previously mentioned, these false positives can be filtered out, for example using volume thresholding, thereby reducing the risk that the presented candidate follicles and their average diameters are obscured by such false positives.

In a preferred embodiment, the segmenting the detected candidate follicles to determine an average diameter for each candidate follicle further comprises defining a seed point for each follicle in the plurality of 2-D ultrasound images, and for each seed point, applying an adaptive region growing algorithm to the plurality of 2-D ultrasound images to segment the candidate follicle associated with said seed point. Such an approach provides an accurate estimation of the candidate follicle volume, such that the average diameter of the candidate follicle can be accurately estimated from the estimated candidate follicle volume.

The method may perform the candidate follicle segmentation based on the automatically identified candidate follicles, e.g. after removal of the false positives as explained above. Alternatively or additionally, the method may further comprise receiving a user-defined additional seed point and applying an adaptive region growing algorithm to the plurality of 2-D ultrasound images to segment the candidate follicle associated with said user-defined additional seed point, thereby facilitating further improvements of the ovarian evaluation by allowing a user to augment the set of seed points created by the method, e.g based on a user evaluation of one or more ultrasound images in the ultrasound scan under evaluation. Such user augmentation of the automatically detected set of seed points is not limited to user-added seed points. In a further embodiment, the method further comprises receiving a user-identified existing seed point and deleting the user-identified existing seed point from the defined seed points, such that the user can remove seed points from the set of defined seed points, for example where it is clear to the user that the seed point does not correspond to an actual follicle.

A further improvement in the accuracy of the candidate follicle evaluation may be obtained by the method further comprising determining a form factor of a pixel area in the plurality of 2-D ultrasound images obtained with the adaptive region growing algorithm during the segmenting of the candidate follicle; and rejecting the candidate follicle if said form factor is below a defined form factor threshold, as this may be indicative of an unreliable segmentation or a further false positive.

The segmentation of the candidate follicles based on the respective seed points may lead to a plurality of segmented candidate follicles in which at least some candidate follicles are at least partially overlapping. This may be an indication of an imaging artefact in which the same candidate follicle is represented multiple times, e.g. at least twice, within this plurality, for example due to the algorithm creating multiple fragments due to the presence of systemic and/or operator-dependent artefacts in the plurality of 2-D ultrasound images. In order to remove such duplicates, the method may further comprise determining an area of overlap between overlapping segmented candidate follicles; and deleting the overlapping segmented candidate follicle having the smaller average diameter if said area of overlap exceeds a defined overlap threshold as in such a scenario it is more likely than not that such overlapping candidate follicles are in fact the same candidate follicle, in which case the smaller of the overlapping candidate follicles is most likely to be the artefact.

In an embodiment, determining an average diameter for each candidate follicle within the detected ovary comprises determining an average diameter of a candidate follicle portion in each 2-D ultrasound image comprising a portion of the candidate follicle; selecting the 2-D ultrasound image having the largest average diameter of the follicle portion; and selecting said largest average diameter as the average diameter of the candidate follicle. This is a straightforward manner of obtaining an accurate average diameter for the candidate follicle.

The success of the respective embodiments of the method of the present invention relies on the clinician providing a pair of ultrasound scans, e.g. an AP scan and a LM scan, which are at least approximately orthogonal to each other in terms of the direction in which the ultrasound probe has been guided across a vaginal region of the female patient in order to obtain significantly different viewing angles of the ovary under investigation. It will be understood that if such viewing angles become too similar, the likelihood of success of the method in identifying the actual diameters of the follicles as previously explained is reduced, as when the viewing angles of the two scans become too similar, inter-observer variability may be insufficiently reduced and the largest diameter of the dominant follicle may be not accurately captured. Therefore, in a particularly advantageous embodiment the method further comprises determining at least one of ovarian rotation and truncation in the detected ovary of each scan of the pair of 2-D (two-dimensional) transvaginal ultrasound scans. In this manner, the sonographer can be warned that the scans are of insufficient quality, such that the sonographer can repeat the one or more scans in order to improve their quality, i.e. the desired capturing of the ovary within the scan. In this context, it should be understood that ovarian rotation refers to the rotation of the ovary between different image frames of the scan, which is indicative of a change in scan direction of the ultrasound probe during acquisition of the scan.

According to a further aspect, there is provided a computer program product comprising a computer readable storage medium having computer readable program instructions embodied therewith for, when executed on a processor arrangement of an ultrasound image processing device, cause said processor arrangement to implement the method of any of the herein described embodiments. Such a computer program product for example may be used to upgrade existing ultrasound image processing devices, thereby improving the quality of the evaluation of ovarian ultrasound scans with such devices.

According to yet a further aspect, there is provided an ultrasound image processing device comprising a processor arrangement adapted to implement the method of any of the herein described embodiments. Such an ultrasound image processing device therefore is capable of providing an improved quality evaluation of 2-D transvaginal ovarian ultrasound scans by providing a more reliable overview of the candidate follicles within the evaluated ovary.

The ultrasound imaging processing device may be configured to implement the method according to embodiments of the present invention by virtue of a processor arrangement specifically designed to implement the method, e.g. a processor arrangement including an ASIC or the like, where at least part of the method is hard-coded into the processor design. Alternatively, the ultrasound image processing device may further comprise the computer program product according to embodiments of the present invention, wherein the processor arrangement is adapted to execute the computer readable program instructions embodied with said computer program product, in which case the processor arrangement may include a generic processor programmable by the computer readable program instructions.

According to yet a further aspect, there is provided an ultrasound imaging system comprising the ultrasound image processing device according to any of the herein described embodiments and an ultrasound probe for providing the ultrasound image processing device with said one or more transvaginal ultrasound scans.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
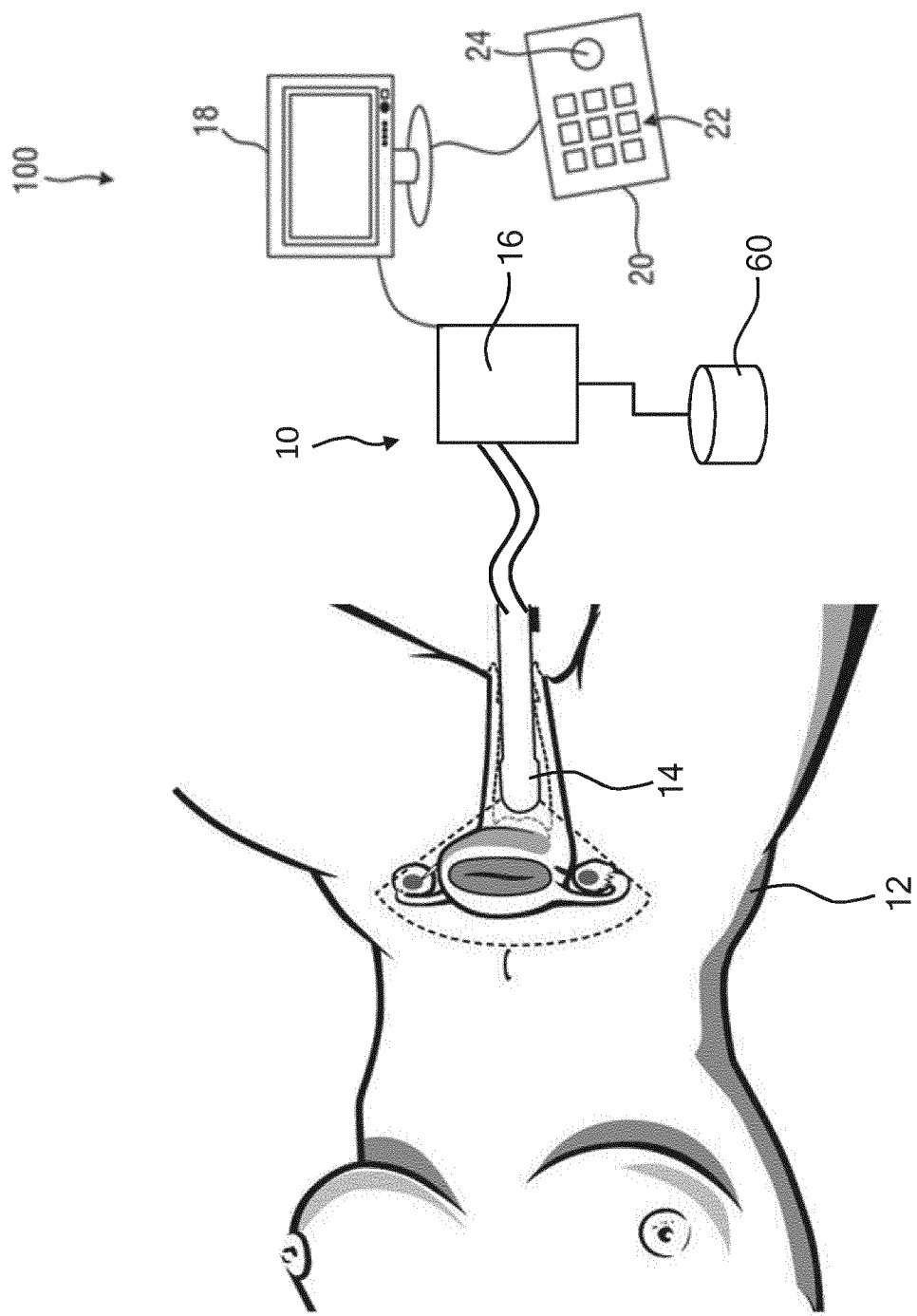
FIG. 1 shows a schematic representation of an ultrasound imaging system in use to scan a part of a patient's body.

It should be understood that the Figures are merely schematic and are not drawn to scale. It should also be understood that the same reference numerals are used throughout the Figures to indicate the same or similar parts.

FIG. 1 shows a schematic illustration of an ultrasound system 100, in particular a medical two-dimensional (2D) ultrasound imaging system. The ultrasound system 100 may be applied to inspect a volume of an anatomical site, in particular an anatomical site of a patient 12 over time, such as a vaginal region of a female patient as shown, e.g. to monitor the effectiveness of a fertility treatment administered to the patient. The ultrasound system 100 comprises an ultrasound probe 14 having at least one transducer array having a multitude of transducer elements for transmitting and/or receiving ultrasound waves. In one example, each of the transducer elements can transmit ultrasound waves in form of at least one transmit impulse of a specific pulse duration, in particular a plurality of subsequent transmit pulses. The transducer elements may be arranged in a linear (one-dimensional) array in case of a 2D ultrasound system 100. In accordance with the present invention and as shown in FIG. 1, the ultrasound probe 14 is suitable for performing a transvaginal ultrasound scan on a female patient, as will be explained in further detail below.

Further, the ultrasound system 100 may comprise a medical ultrasound image processing device 10 comprising a processor arrangement including an image reconstruction unit 16 that controls the provision of a 2D image sequence via the ultrasound system 100. As will be explained in further detail below, the image reconstruction unit 16 may control not only the acquisition of data via the transducer array of the ultrasound probe 14, but also signal and image processing that form the 2D image sequence out of the echoes of the ultrasound beams received by the transducer array of the ultrasound probe 14. Such a medical ultrasound image processing device 10 for example may be a console or the like to which the ultrasound probe 14 may be connected.

The ultrasound system 100 may further comprise a display device 18 (from here on also referred to as display 18) for displaying the 2D image sequence to the user. Still further, an input device 20 may be provided that may comprise keys or a keyboard 22 and further inputting devices, for example a trackball 24. The input device 20 might be connected to the display 18 or directly to the image reconstruction unit 16. In some embodiments, at least one of the input device 20 and the display 18 may be integral to the medical ultrasound image processing device 10.

The ultrasound system 100 may further comprise a data storage arrangement 60, e.g. one or more memory devices, hard disks, optical discs, or the like, in which the image reconstruction unit 16 may store image frames and image frame processing data, e.g. for evaluation at a later date. The data storage arrangement 60 may be integral to the medical ultrasound image processing device 10 or may be connected to the may be integral to the medical ultrasound image processing device 10 in a peer-to-peer manner or across a network as is well-known per se.

Figure 2:
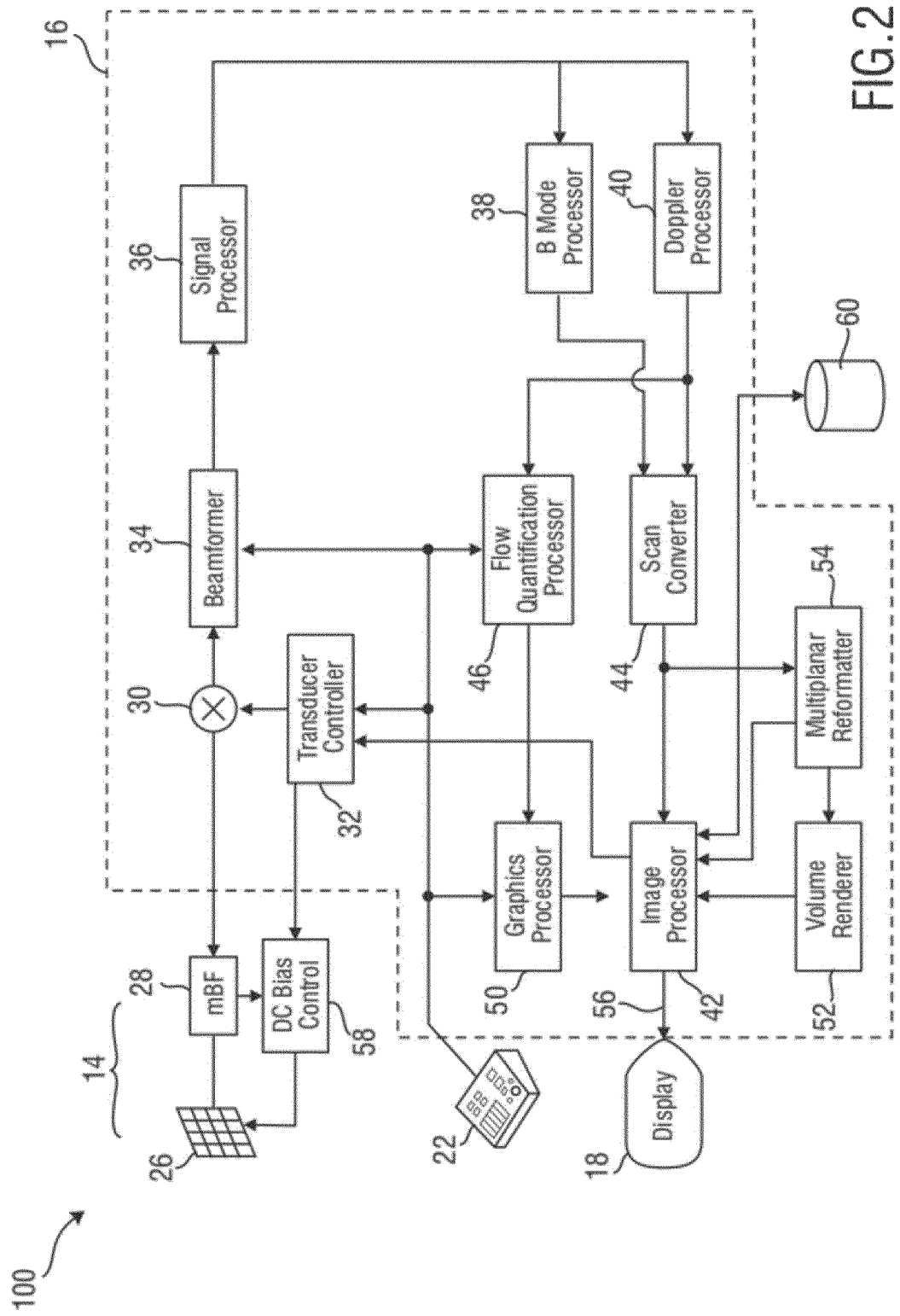
FIG. 2 shows a schematic block diagram of an embodiment of an ultrasound imaging system with an array transducer.

FIG. 2 illustrates a schematic block diagram of the ultrasound system 100. The ultrasound probe 14 may, for example, comprise a CMUT transducer array 26. The transducer array 26 may alternatively comprise piezoelectric transducer elements formed of materials such as PZT or PVDF. The transducer array 26 for example may comprise a one-dimensional array of transducer elements capable of scanning in two dimensions for 2D imaging.

The transducer array 26 is coupled to a microbeamformer 28 in the probe which controls transmission and reception of signals by the CMUT array cells or piezoelectric elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer 28 may be coupled by a probe cable to a transmit/receive (T/R) switch 30 which switches between transmission and reception and protects the main beamformer 34 from high energy transmit signals when a microbeamformer 28 is not used and the transducer array 26 is operated directly by the main beamformer 34.

The transmission of ultrasonic beams from the transducer array 26 under control of the microbeamformer 28 is directed by a transducer controller 32 coupled to the microbeamformer 28 by the T/R switch 30 and the main system beamformer 34, which receives input from the user's operation of the user interface or control panel 22. One of the functions controlled by the transducer controller 32 is the direction in which beams are steered and focused. Beams may be steered straight ahead from (orthogonal to) the transducer array 26, or at different angles for a wider field of view. The transducer controller 32 can be coupled to control a DC bias control 58 for a CMUT array. The DC bias control 58 sets DC bias voltage(s) that are applied to the CMUT cells of such a CMUT array.

The partially beamformed signals produced by the microbeamformer 26 on receive are coupled to the main beamformer 34 where partially beamformed signals from individual patches of transducer elements are combined into a fully beamformed signal. For example, the main beamformer 34 may have 128 channels, each of which receives a partially beamformed signal from a patch of dozens or hundreds of CMUT transducer cells or piezoelectric elements. In this way the signals received by thousands of transducer elements of the transducer array 26 can contribute efficiently to a single beamformed signal.

The beamformed signals are coupled to a signal processor 36, which may form part. The signal processor 36 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and/or microbubbles comprised in a contrast agent that has been pre-administered to the body of the patient 12. The signal processor 36 may also perform additional signal enhancement such as speckle reduction, signal compounding, and noise elimination. The bandpass filter in the signal processor 36 can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be transferred to a B mode processor 38 and a Doppler processor 40. The B mode processor 38 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.)

The Doppler processor 40 may process temporally distinct signals from tissue movement and blood flow for the detection of the motion of substances such as the flow of blood cells in the image field. The Doppler processor 40 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 40 may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors 38, 40 may then be transferred to a scan converter 44 and a multiplanar reformatter 54. The scan converter 44 arranges the echo signals in the spatial relationship from which they were received in a desired image format. For instance, the scan converter 44 may arrange the echo signal into a two dimensional (2D) sector-shaped format. The scan converter 44 can overlay a B mode structural image with colors corresponding to motion at points in the image field with their Doppler-estimated velocities to produce a color Doppler image which depicts the motion of tissue and blood flow in the image field.

In addition to being used for imaging, the blood flow values produced by the Doppler processor 40 and tissue structure information produced by the B mode processor 38 may be transferred to a quantification processor 46 forming part of the processor arrangement. This quantification processor 46 may produce measures of different flow conditions such as the volume rate of blood flow as well as structural measurements such as the sizes of organs and gestational age. The quantification processor 46 may receive input from the user control panel 22, such as the point in the anatomy of an image where a measurement is to be made. Output data from the quantification processor 46 may be transferred to a graphics processor 50 forming part of the processor arrangement for the reproduction of measurement graphics and values with the image on the display 18. The graphics processor 50 can also generate graphic overlays for display with the ultrasound images. These graphic overlays can contain standard identifying information such as patient name, date and time of the image, imaging parameters, and the like, as will be explained in more detail below. For these purposes the graphics processor 50 may receive input from the user interface 22, such as patient name. The user interface 22 may be coupled to the transmit controller 32 to control the generation of ultrasound signals from the transducer array 26 and hence the images produced by the transducer array and the ultrasound system.

Again, it shall be noted that the aforementioned ultrasound system 100 only has been explained as one possible example for an application of the medical ultrasound image processing device 10. It shall be noted that the aforementioned ultrasound system 100 does not have to comprise all of the components explained before. On the other hand, the ultrasound system 100 may also comprise further components, if necessary. Still further, it shall be noted that a plurality of the aforementioned components does not necessarily have to be realized as hardware, but may also be realized as software components. A plurality of the aforementioned components may also be comprised in common entities or even in one single entity and do not all have to be realized as separate entities, as this is schematically shown in FIG. 2.

Figure 3:
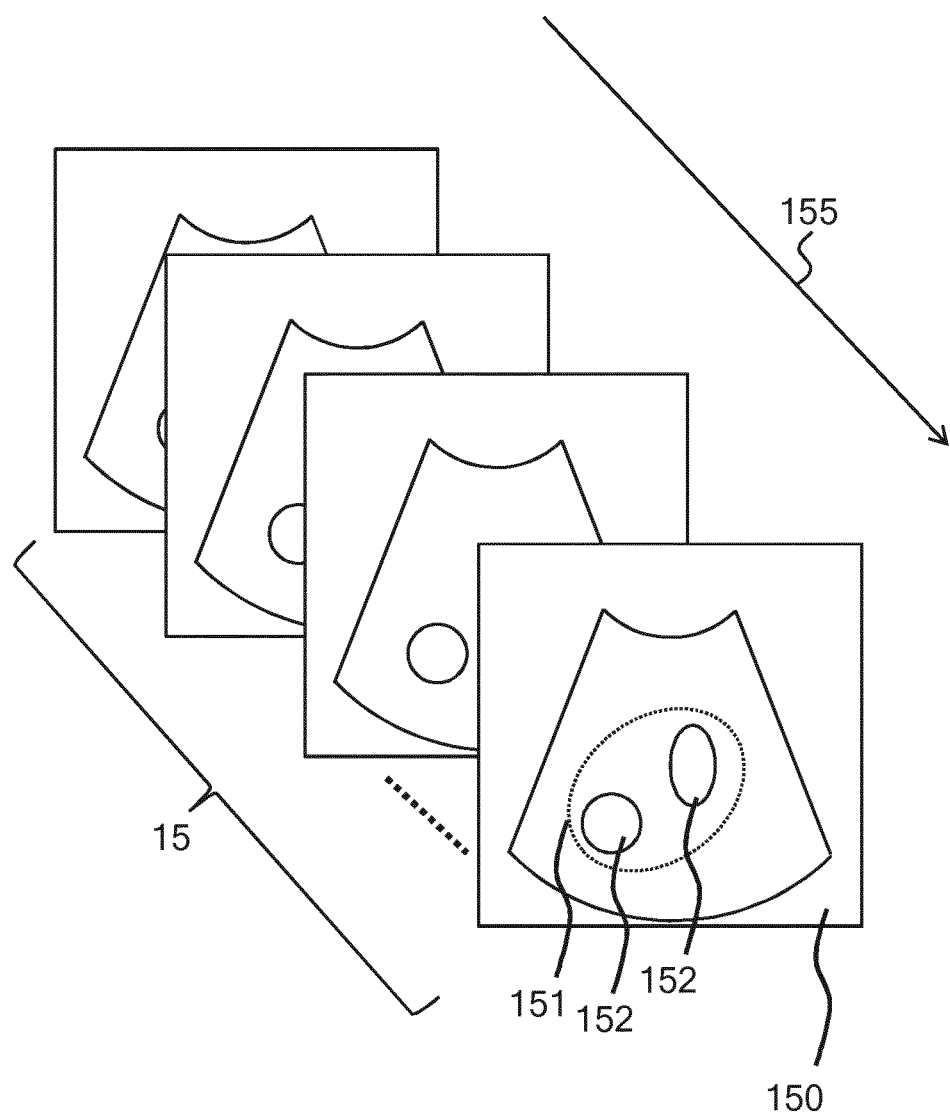
FIG. 3 schematically depicts a sequence of 2-D ultrasound images visualizing at least part of an ovary of a female patient.

FIG. 3 schematically depicts a sequence or scan 15 of 2-D ultrasound images 150, which sequence is typically captured by a sonographer moving the ultrasound probe 14 in a direction 155 across a region of interest of a patient, such that the ultrasound probe 14 periodically captures a 2-D ultrasound image 150 such that the sonographer can obtain an impression of a body volume of interest, slices of which are captured by the respective ultrasound images 150. For example, in case of a transvaginal scan of a female patient the scan 15 of 2-D ultrasound images 150 may provide a visualization of at least part of an ovary 151 of the female patient, which ovary 151 typically comprises a number of follicles 152, which for example may show up in the 2-D ultrasound images 150 as dark regions, i.e. regions having a particular pixel value, within the boundary of the ovary 151, which boundary for example may be recognized as an ellipsoid region within the 2-D ultrasound images 150.

In example embodiments of the present invention, the 2-D ultrasound images 150 may be captured in the XY plane, with the probe 14 being moved in the Z direction 155, such that each image 150 has a label or frame number associated with the Z direction 155, thereby yielding a sequence or stack of 2-D images 150 in the XY plane. However, it should be understood that the present invention is not limited to processing of a sequence of 2-D images. In alternative embodiments, the primary input of the sequence 15 of ultrasound images 150 may be processed to construct (render) a 3-D volumetric image, e.g. using existing suitable algorithms such as the freehand 3d algorithm by way of non-limiting example, in which case the Z-direction 15 becomes the Z-coordinate of such a volumetric image, with the further processing in accordance with embodiments of the present invention as described in more detail below being performed on the volumetric image.

As previously explained, a clinician such as a gynecologist, sonologist or the like may wish to evaluate the scan 15 to determine the number of follicles 152 within the ovary 151, as well as the diameter of such follicles, e.g. to identify antral follicles having an average diameter of 2-9 mm or more generally, to identify follicles having an average diameter of 7-25 mm. Other sized target follicles of course may be the subject of alternative investigations. The clinician may have a number of reasons for such an evaluation, such as the assessment of the fertility of the female patient and/or monitoring of the ovulation cycle of the female patient, as during the ovulation cycle one or more-follicles 152 may develop, i.e. increase in diameter. During such ovarian stimulation, multiple follicles 152 may be recruited and grow, although the growth rate of such follicles is typically different to each other. The development of the number of follicles 152 and their respective growth rates may be used by the clinician to tailor a treatment regime to the individual needs of the female patient in order to maximize the chance of successful fertilization. The clinician may support such clinical findings by further monitoring thickness changes to the endometrium, as it is well-known per se that such thickness changes correlate with the menstrual cycle and can be used as a marker of the relevant hormonal levels within the female patient, thereby correlating with assisted reproductive technology success rates.

Previously, such ovarian evaluation including follicles size monitoring typically was a manual process in which a sonographer attempted to obtain the 2-D ultrasound image showing the largest follicle diameter by moving the ultrasound probe 14 in arbitrary directions based on the visual feedback provided by already captured 2-D ultrasound images 150 as displayed on the display 18. As will be appreciated by the skilled person, this is a trial and error process for each follicle with a high degree of inter-operator variability, such that it often proved difficult to consistently obtain reliable 2-D ultrasound data, which is problematic in terms of patient assessment and monitoring and may be uncomfortable and stressful to the patient in a scenario where the scan 15 has to be repeated several times in order to obtain an acceptable or useful sequence of 2-D ultrasound images 150.

Figure 5:
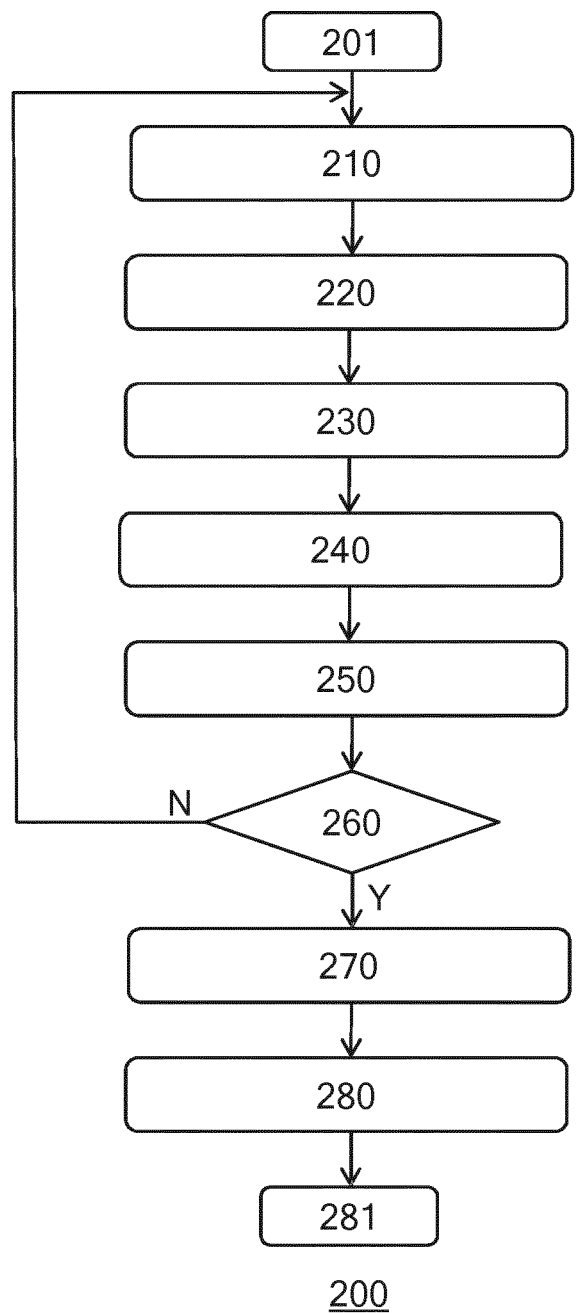
FIG. 5 is a flowchart of an example embodiment of a computer-implemented method for determining an ovarian follicle count and size.

Embodiments of the present invention address this problem by providing an automated solution of evaluating a transvaginal 2-D ultrasound scan in which the ultrasound image processing device 10, i.e. the processor arrangement of the ultrasound image processing device 10, is configured to automatically evaluate an ovarian section captured in such a transvaginal 2-D ultrasound scan and provide its user, e.g. a sonographer or a clinician such as a sonologist or gynaecologist with an overview of the detected candidate follicles 152 in the scan 15. In other words, the ultrasound image processing device 10 is configured to implement a method 200, a flowchart of which is depicted in FIG. 5.

Figure 4:
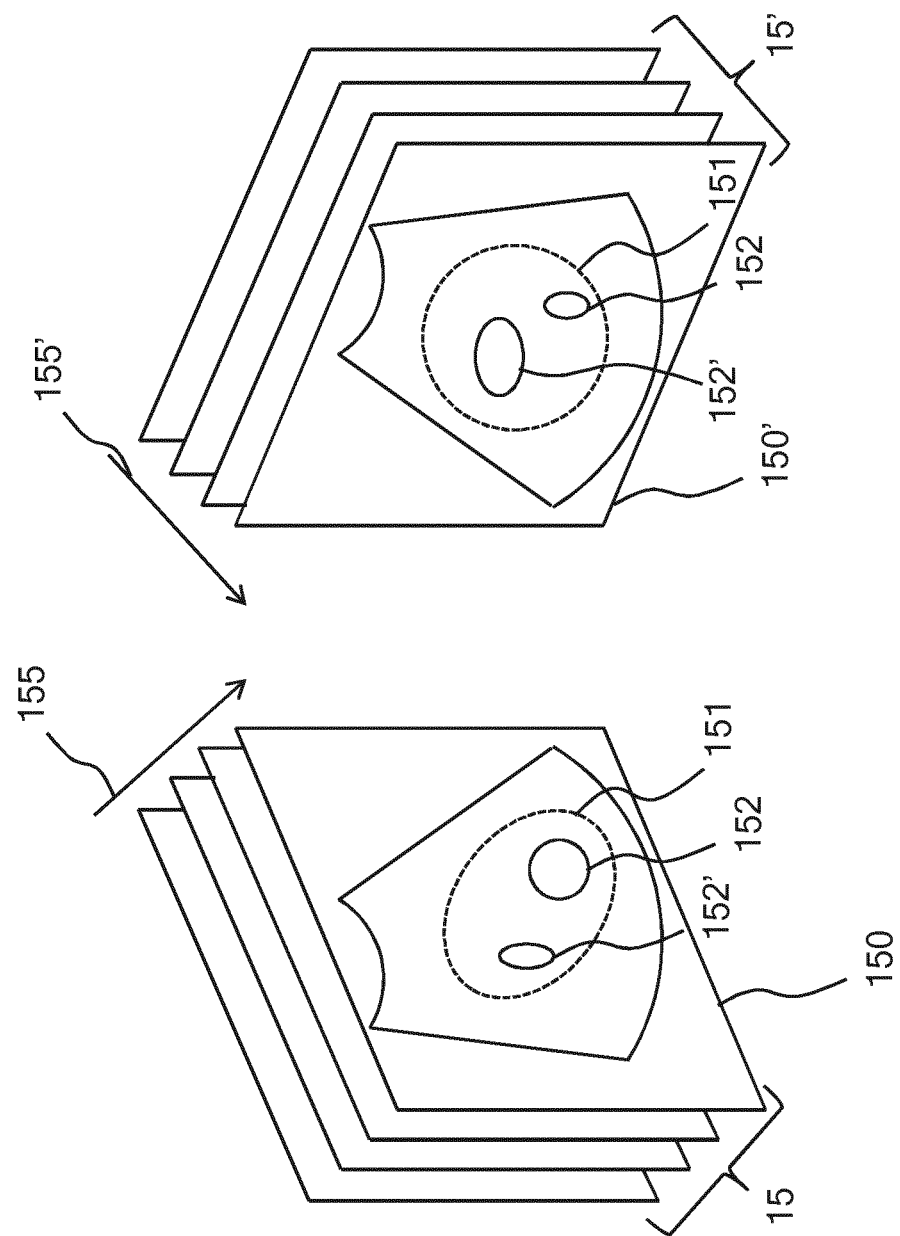
FIG. 4 schematically depicts an orthogonal pair of sequences of 2-D ultrasound images each visualizing at least part of an ovary of a female patient in accordance with an embodiment.

In order to facilitate the automation of this evaluation, the sonographer or clinician has to perform at least one transvaginal scan 15 and preferably performs a pair of transvaginal scans 15, 15' on the female patient as schematically depicted in FIG. 4. The scans 15, 15' should be performed such that the directions 155, 155' in which the ultrasound probe 14 is moved across a region of interest of the female patient are largely orthogonal, i.e. at least approximately orthogonal. In the context of the present application, where reference is made to 'at least approximately orthogonal', it should be understood that this is meant to cover scenarios in which the angle between the respective directions 155, 155' is within the range of 70-110°, preferably within a range of 80-100° and more preferably is about 90° in order to maximize the difference in viewing angles of the ovary 151 or part thereof captured in the scans 15, 15'. For example, the scan 15 of 2-D ultrasound images 150 may be performed in an anterior to posterior direction, which will also be referred to as a horizontal scan, whereas the further scan 15' of 2-D ultrasound images 150' may be performed in a lateral to medial direction, which will also be referred to as a vertical scan 15'. This assists in identifying the candidate follicle 152 having the largest average diameter within the ovary 151 regardless of the orientation of this follicle within the ovary.

A particular advantage of performing such orthogonal scans 15 is that the ovary 151 and candidate follicles 152, 152' therein is visualized under different angles, thereby increasing the chance that the largest diameter follicle is correctly identified and an accurate estimate of its diameter can be obtained with greater confidence. This is schematically depicted in FIG. 4, in which the ovary 151 and candidate follicles 152, 152' therein have different shapes in the respective scans 15, 15'. This for example typically arises with ellipsoid structures, where the first scan 15 may be performed approximately along one of the major and minor axis of the ellipsoid structure whilst the second scan 15' is performed along the other of the major and minor axis of the ellipsoid structure. Depending on which axis is followed, the appearance and size of the ellipsoid structure may be perceived differently by the clinician, as symbolized by the different shapes of the follicles 152 and 152' respectably in the scans 15 and 15'. However, it should be understood that in some embodiments of the present invention the automated follicle count and size detection may be performed on a single scan 15 as this already may provide an accurate enough estimate of the desired follicle characteristics within the ovary 151.

Upon receiving the one or more scans 15, 15', which may be at least temporarily stored in the data storage arrangement 60, the ultrasound image processing device 10 progresses from the start 201 of the method 200 to operation 210 in which one of the scans 15, 15' of 2-D ultrasound images 150, 150' is selected for automatic evaluation. The selected scan is subsequently processed in operation 220 in which an approximate volume image may be constructed from the respective 2-D ultrasound images in the selected scan. The construction of such approximate volume images from a sequence of 2-D ultrasound images is a well-known technique and as such is not explained in further detail for the sake of brevity only. The approximate volume image subsequently is evaluated in operation 230 to detect the outline of the ovary 151 within the approximate volume image as well as all candidate follicles 152, 152' within the ovary 151. Such detection for example may include the deployment of an ellipsoid identification algorithm to detect the ovarian outline within the approximate volume image and ellipsoid regions within the ovarian outline which may be candidate follicles 152, 152' within the ovary 151. Other suitable algorithms for such detection of the ovary 151 and the possible follicles 152 within the ovary 151 in the approximate volume image will be immediately apparent to the skilled person, e.g. by identification of low intensity regions within the imaging area and fitting an ellipsoid function to each of the identified regions. Each of the candidate follicles 152 may be labelled by the method 200, which labels may be utilized by the method 200 in the further processing of the candidate follicles 152.

Figure 6:
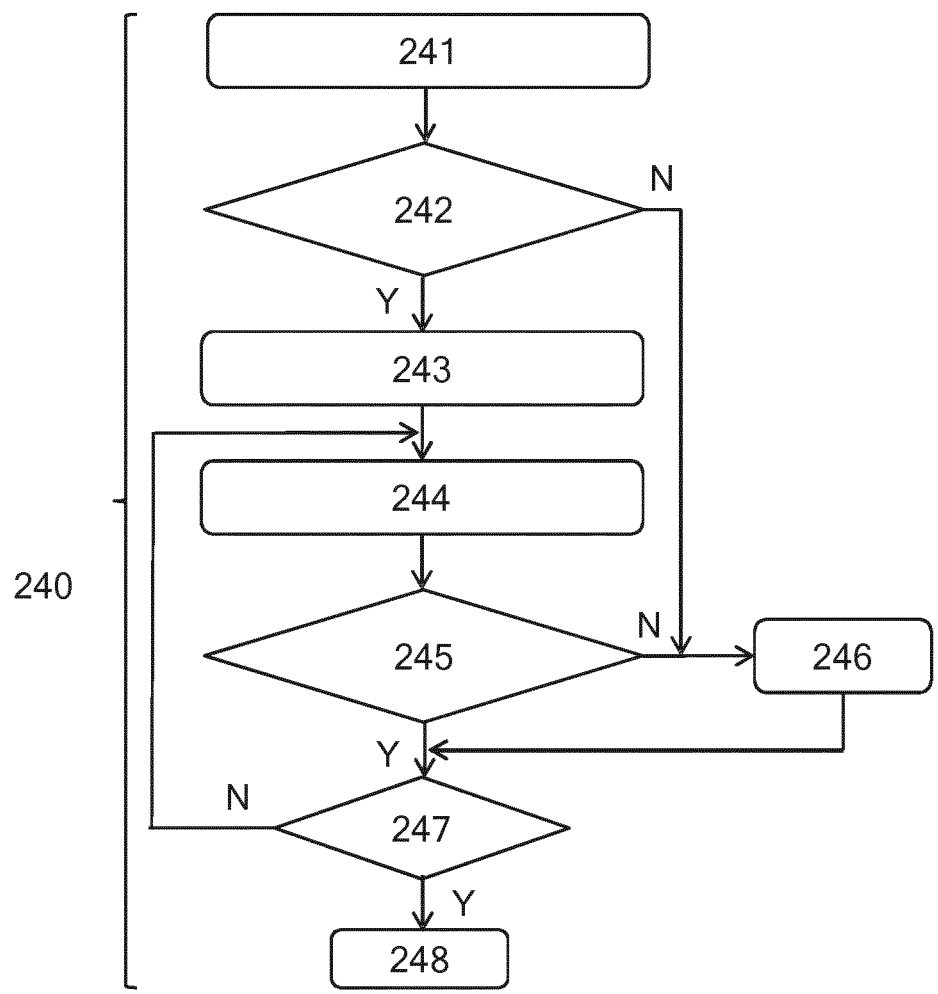
FIG. 6 is a flowchart of an aspect of an example embodiment of a computer-implemented method for determining an ovarian follicle count and size in more detail.

Next, the (labelled) candidate follicles 152 are segmented in operation 240, which is explained in more detail with the aid of the flowchart depicted in FIG. 6. In sub-operation 241, the total number of voxels or volume of each region connected to a particular label is identified and compared against a volume threshold in sub-operation 242 to determine if the possible follicle 152 corresponding to the total number of voxels or volume is a false positive. Specifically, if the total number of voxels or volume is below the defined volume threshold, the possible follicle 152 associated with that label is considered a false positive and is disregarded in the subsequent segmentation of the follicles 152.

Figure 7:
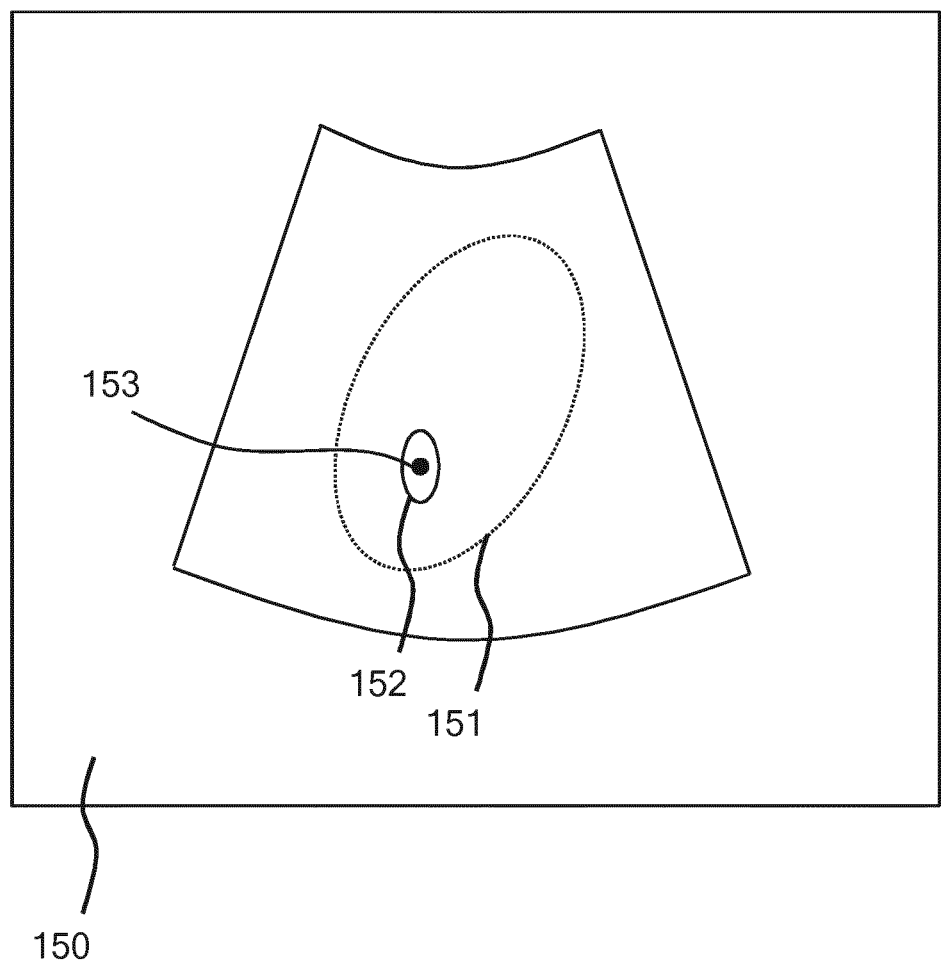
FIG. 7 schematically depicts a 2-D ultrasound image for processing by an example embodiment of a computer-implemented method for determining an ovarian follicle count and size.
Figure 8:
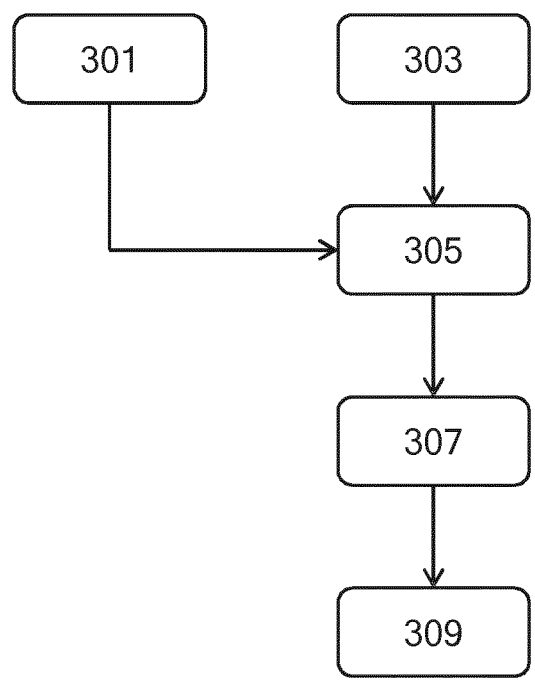
FIG. 8 is a flowchart of another aspect of an example embodiment of a computer-implemented method for determining an ovarian follicle count and size in more detail.

For the follicles 152 that are considered true candidate follicles, i.e. have a total number of voxels or volume at least matching the defined volume threshold, the segmentation operation 240 proceeds to the sub-operation 243 in which a seed point 153 for the true follicle segment 152 is generated, as schematically depicted in FIG. 7. FIG. 8 is a flow chart of the generation method of such seed points 153 in more detail. In operation 301, the seed point generation algorithm is provided with the list of labels classified as candidate follicles, which operation may be performed in parallel or sequentially with operation 303 in which the scan 15 (or 15') of 2-D ultrasound images 150 (or 150') is provided to the algorithm. In operation 305, for each of the labels classified as candidate follicle, the lowest pixel value associated with the corresponding connected label may be determined, after which in operation 307 the 2-D ultrasound image frame 150 containing the largest number of pixels having this lowest pixel value associated with the label is found. This frame may be thus identified as the frame in which the seed point 153 of the candidate follicle 152 is to be contained. The pixel coordinates, e.g. (X, Y) coordinates of the lowest pixel value pixels in this identified 2-D ultrasound image frame 150 may be obtained and the median (average) of these pixel coordinate values may be determined in operation 309 to obtain the coordinates of the seed point 153 for the follicle 152. In this manner, a list of seed points expressed in any suitable coordinate form may be compiled for all true potential follicles 152, i.e. the follicles excluding the determined false positives.

Figure 9:
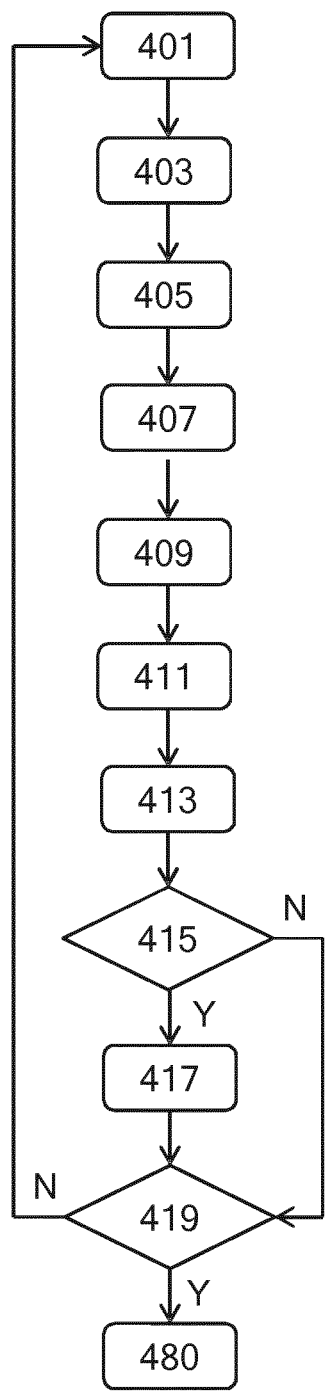
FIG. 9 is a flowchart of yet another aspect of an example embodiment of a computer-implemented method for determining an ovarian follicle count and size in more detail.

The thus obtained seed points 153 may be used in sub-operation 244 in which each associated follicle 152 is segmented in three dimensions, e.g. in the XY, YZ and XZ 'planes' using an adaptive growing algorithm, as will be explained in further detail with the aid of FIG. 9, which depicts a flowchart of an example embodiment of this segmentation algorithm. It is reiterated here that in embodiments in which this sub-operation is performed on a sequence of 2-D images 150, 'Z' identifies the direction in which the image frames in the XY plane have been captured. In a preferred embodiment, the primary input of the ultrasound image processing device according to embodiments of the present invention is a sequence 15 of 2D ultrasound frames 150 scanned in a particular direction 155. This primary input can be either used 'as is' or it can be further processed in any known manner to construct a pseudo 3D volume. When the sequence 15 is used 'as is', 'Z' may be the frame number of the individual image frames, whereas Z is the 'Z' co-ordinate in case of pseudo 3D volume.

For a given candidate follicle 152 as identified in operation 401 by its seed point 153, the segmentation algorithm obtains a first image plane of the approximate volume image in operation 403, e.g. the YZ plane, after which this image plane (approximate 2-D slice) is processed in operation 405, as will be explained in more detail below. This is repeated in operation 407 in which the second image plane of the approximate volume image is obtained, e.g. the XZ plane, after which this image plane (approximate 2-D slice) is processed in operation 409 and in operation 411 in which the third image plane of the approximate volume image is obtained, e.g. the XY plane, after which this image plane (approximate 2-D slice) is processed in operation 413.

In operation 415 it is checked if the segmentation of the image in the XY plane has been successful. If this is not the case, the image and associated listing are rejected and it is checked in operation 419 if further candidate follicles 152 and their associated seed points 153 are to be processed in this manner. If this is the case, the method returns to operation 401 in which the next candidate follicle 152 and its associated seed point 153 is retrieved for processing as explained above. If on the other hand it is determined in operation 415 that the segmentation in the XY plane has been successful, the segmentations of all three planes are combined in operation 417 to form a solid follicle segment, after which this solid follicle segment and its measurements may be added to a list to be presented to the user of the ultrasound system 100 in operation 480 once all seed points 153 have been processed in this manner as will be explained in further detail below.

For each segmentation, the seed point 153 may be repositioned to the centroid of the follicle segmentation in order to increase the accuracy of the segmentation operation. Prior to application of the adaptive growing algorithm, some noise filtering may be applied to the approximate volume image, for example a Gaussian filter and Otsu thresholding, in order to reduce the image noise and to enhance the contrast of the candidate follicles 152, 152' against their background.

In image processing operations 405, 409 and 413, an adaptive region growing algorithm may be applied to obtain the segmentation of the approximate volume image slice under investigation. Such an adaptive growing algorithm for example may be governed by a form factor (FF) condition according to the equation below:

$$FF = \frac{4\pi A}{P^2}$$

In this equation, A is the follicle area (in mm) in the segmentation and P is the follicle perimeter (in mm) in the segmentation. The adaptive region growing algorithm iteratively increases the pixel value range, e.g. using a region growing threshold, and calculates the form factor FF after each iteration. Once the form factor FF has assumed a constant minimum value, e.g. a value larger than a defined form factor threshold value, over a predefined number of iterations, e.g. three or more iterations, the iterative process is terminated, after which the region growing threshold applied to the final iteration may be used to segment the follicle 152 for a final time.

The thus obtained segmented follicle 152 may be subjected to a morphological opening transformation in order to sharpen the boundaries of the segmented follicle 152, i.e. to reduce the noise. As is well-known per se, a morphological opening transformation of an image comprises an erosion operation in which all pixels covered by a defined kernel keep their original value if this value equals a defined value, e.g. '1', otherwise all pixels are eroded to a further value, e.g. '0'. The kernel is systematically migrated across the image to perform the erosion operation. The erosion operation is followed by a dilation operation in which all pixels overlapped by the kernel are given a defined value if at least one of the pixels has the defined value. After the morphological operation, the transformed image is checked to see if at least one segment contains the seed point 153. If not, the follicle 152 is rejected in sub-operation 246, otherwise the transformed follicle segment(s) containing the seed point is subjected to a further determination of its form factor in sub-operation 245 in order to find the average diameter of the candidate follicle 152. The segmentation process is repeated for a set of images near to the seed point in each of the XY, YZ and XZ planes in order to find the largest follicle diameter of the candidate follicle 152 in that plane. If the follicle 152 can be segmented in the XZ and YZ planes but not in the XY plane then an average diameter cannot be found for that follicle since for the clinician, the average diameter corresponds to the XY plane. In such cases, the candidate follicle 152 is also rejected. It is checked in sub-operation 247 if all true follicles 152 have been segmented in this manner. If this is not the case, the segmentation operation returns to sub-step 244 in which the next true follicle 152 is segmented and this process is repeated until all true follicles 152 have been segmented in this manner, after which operation 240 terminate in sub-operation 248.

Figure 10:
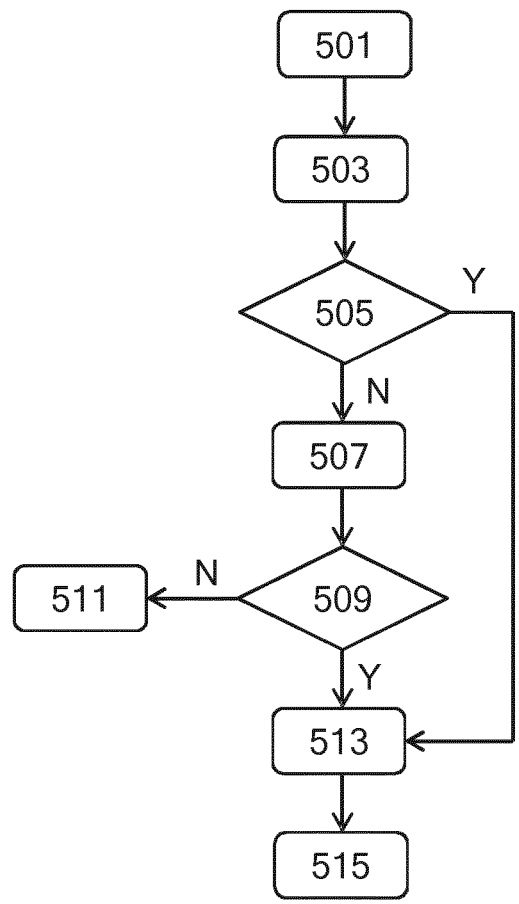
FIG. 10 is a flowchart of yet another aspect of an example embodiment of a computer-implemented method for determining an ovarian follicle count and size in more detail.

In an example embodiment, the candidate follicle assessment may be performed according to the flowchart depicted in FIG. 10. The method starts in operation 501 with receiving the retrieved approximate image volume slice, e.g. a slice in the YZ, XZ or XY plane as previously explained, after which the aforementioned adaptive region growing algorithm may be applied to the retrieved approximate image volume slice in operation 503. In operation 505, it is checked if the calculated form factor at least meets a defined minimum form factor to check if the candidate follicle likely is a true follicle. If this is not the case, the method may proceed to operation 507 in which neighboring approximate image volume slices in the same plane are segmented and evaluated in operation 509 to determine if their calculated form factor at least meets this defined minimum form factor. If this is also not the case for these slices, the candidate follicle 152 and its seed point 153 are rejected in operation 511. On the other hand, if in either operation 505 and 509 it is determined that the determined form factor at least meets the defined minimum form factor, the method proceeds to operation 513 in which a defined number of neighboring image volume slices in the same plane, e.g. 25 neighboring slices on either side of the approximate volume slice under investigation, are segmented and subjected to the adaptive region growing algorithm in order to obtain an approximate solid follicle segment based on the selected seed point 153, after which the largest diameter of the candidate follicle 152 in the XY plane may be identified in the set of segmented frames in operation 515 for presentation to the user as explained in more detail below.

Optionally, after obtaining all the follicular segments from their seed points 153, the overlap between each of the follicle segments may be calculated and compared against a defined overlap threshold in optional operation 250. Specifically, if the overlap area between such adjacent follicle segments is larger than the defined overlap threshold, the follicle 152 with the smaller largest average diameter may be considered a duplicate of the follicle 152 with the larger largest average diameter with which it overlaps, in which case the follicle 152 with the smaller largest average diameter may be removed from the evaluation results as well as from the list of labels generated in operation 230.

The resulting determined largest average diameters of the respective accepted segmented follicles 152 may be listed in an organized manner, such as in a descending order such that the follicle 152 having the largest average diameter is top of the list or alternatively in an ascending order such that the follicle 152 having the smallest average diameter is top of the list.

It is subsequently determined in operation 260 if two (approximately orthogonal) scans 15, 15' have been performed as explained above. If only a single scan has been performed, the method 200 may proceed to operation 280. Otherwise, the method 200 reverts back to operation 210 in which the next (i.e. the second) scan is selected for processing. After both scans 15, 15' have been processed in this manner, the method 200 proceeds to optional operation 270 in which the evaluation results of both scans are compared, e.g. by comparing the compiled lists of determined follicle diameters, in order to identify the scan comprising the dominant candidate follicle 152 having the largest average diameter, which scan subsequently is selected as the scan to be used for evaluation by the clinician or sonographer. Subsequently, the determined largest average diameters of the segmented follicles 152 of the single scan 15 or of the selected scan in optional operation 270 in case of the capturing of two (approximately orthogonal) scans 15, 15', are presented to the clinician or sonographer in operation 280, for example by displaying the determined largest average diameters of the segmented follicles 152 on the display 18 together with their segmentations, preferably in the form of an ordered list such as a list of descending average follicle diameters such that the clinician or sonographer can readily determine the largest average diameter of the dominant follicle 152 in the selected scan, after which the method 200 terminates in 281.

In an embodiment, the list of follicle diameters may facilitate the user to visualize a particular follicle, e.g. by including hyperlinks or the like for each of the entries in the list. The user may activate the hyperlink by clicking on it, which triggers the display 18 to display the 2-D ultrasound image 150 in which the listed follicle diameter is present. This image may be fused with the final segmentation of the selected follicle, which fusing for example may comprise overlaying the displayed 2-D image with the segmentation result as a highlight, e.g. using different brightness and/or different colours, optionally supplemented by displaying the measurement results of the segmented follicle such as its diameter. In this manner, the clinician can easily navigate to a view of the follicle segments of interest. Many variations to the implementation of the displayed results may of course be considered without departing from the teachings of the present invention.

As previously explained, upon presenting the evaluation results to the clinician or sonographer, the method 200 may further facilitate post-processing of the evaluation results, for example by a user adding new seed points 153 for further evaluation (segmentation) or by removing seed points 153 of follicles 152, e.g. using the user interface 20, for which the user for example has determined that the follicles are not true follicles after evaluation of the 2-D ultrasound images 150, 150' of the selected scan 15, 15'. As will be readily understood by the skilled person, such post-processing may further include reordering the ordered list of segmented follicles 152, e.g. to include user-identified follicles after their automated segmentation following the user-specified seed points of such follicles or to remove user-identified follicles from such an ordered list. Similarly, the label map or list generated in operation 230 may be adjusted accordingly.

In an embodiment, the ultrasound image processing device 10 may be further configured to check the sweep quality of the scans 15, 15', for example to check whether the scans are truncated such that not all of the ovary and the follicles within the ovary have been captured in the scans or to check whether the scans are rotated in the sense that during capturing of the scans the user has changed the propagation direction 155 or 155' of the ultrasound probe 14 during capturing of the scans 15 or 15'. Upon detection of such a truncation or rotation, the ultrasound image processing device 10 may generate a result of the check or evaluation of the sweep quality of the scans, e.g. on the display 20, in order to facilitate the user of the ultrasound probe 14 to rescan the region of interest of the patient 12. The result of the evaluation may be presented in any suitable manner, and may for example take the form of a visual or audible warning signal or the like.

For example, whether a scan 15 or 15' is truncated may be determined based on an evaluation of the position of the follicle seed points 153 within the scan. Specifically, it is checked if any of the follicle segments identified in the approximate volume image contain defined minimum number of boundary pixels, e.g. by determining the number of boundary pixels in the follicle segment and comparing this number against a defined threshold. In the context of the present application, boundary pixels are pixels in the facility of the boundary between the image background and foreground in a 2-D ultrasound image 150 or 150'. If any of the follicle segments at least contains this minimum number of boundary pixels, the scan is classified as truncated.

Alternatively or additionally, a scan 15 or 15' may be classed as rotated based on the mean ellipse deformation tensor of the follicle segmentations in the XZ and YZ planes. Specifically, a scan may be classed as rotated if the follicles appear to be elongated in either of these planes. This for instance may be determined by determining a form factor of the follicle segmentation in the XY plane. If the follicle segmentation in the XY plane is larger than a threshold for that plane and if either of the mean ellipse deformation tensor of the follicle segmentations in the XZ and YZ planes are less than the thresholds defined for their respective planes, the scan is classed as rotated.

According to an aspect of the present invention, a computer program product may be provided comprising a computer readable storage medium having computer readable program instructions (code) embodied therewith for, when executed on the processor arrangement of the ultrasound image processing device 10, cause the processor arrangement 10 to implement any embodiment of the method 200.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor arrangement may be written in any combination of one or more programming languages, including an object oriented programming language such as Java, Smalltalk, C++ or the like and conventional procedural programming languages, such as the "C" programming language or similar programming languages. The program code may execute entirely on the processor arrangement as a stand-alone software package, e.g. an app, or may be executed partly on the processor arrangement and partly on a remote server. In the latter scenario, the remote server may be connected to the ultrasound image processing device 10 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the processor arrangement of the ultrasound image processing device 10, such that the instructions create means for implementing the functions/acts specified in the flowchart and/or block diagram block or blocks. These computer program instructions may also be stored in a computer-readable medium that can direct the ultrasound image processing device 10 to function in a particular manner.

The computer program instructions may be loaded onto the processor arrangement to cause a series of operational steps to be performed on the processor arrangement, to produce a computer-implemented process such that the instructions which execute on the processor arrangement provide processes for implementing the functions/acts specified in the flowchart and/or block diagram block or blocks. The computer program product may form part of the ultrasound image processing device 10, e.g. may be installed on the ultrasound image processing device 10.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A computer-implemented method for determining an ovarian follicle count and size, comprising:
   receiving a pair of 2-D (two-dimensional) transvaginal ultrasound scans, each scan comprising a plurality of 2-D ultrasound images captured along a translation direction of an ultrasound probe used to capture said scan, the respective translation directions being at least approximately orthogonal, and for each of said scans, the method further comprising:
   determining at least one of ovarian rotation and truncation in a detected ovary of each of the 2-D (two-dimensional) transvaginal ultrasound scans;

detecting candidate follicles in the plurality of 2-D ultrasound images of the 2-D transvaginal ultrasound scan, wherein detecting candidate follicles in the plurality of 2-D ultrasound images comprises:
approximating a volume image from the plurality of 2-D ultrasound images;
detecting the ovary in the approximated volume image;
detecting possible candidate follicles within the detected ovary;
determining a volume for each candidate follicle; and
rejecting the candidate follicles that have a determined volume below a defined volume threshold for subsequent segmenting;
segmenting the detected candidate follicles to determine an average diameter for each candidate follicle;
selecting the 2-D transvaginal ultrasound scan including the candidate follicle having the largest average diameter; and
presenting the determined average diameters and the segmentations of the detected candidate follicles of the selected 2-D transvaginal ultrasound scan.

2. The computer-implemented method of claim 1, wherein:
said selecting the 2-D transvaginal ultrasound scan including the follicle having the largest average diameter is based on the determined average diameters.

3. The computer-implemented method of claim 1, wherein detecting candidate follicles in the plurality of 2-D ultrasound images further comprises labelling the detected candidate follicles for further processing.

4. The computer-implemented method of claim 1, wherein segmenting the detected candidate follicles to determine an average diameter for each candidate follicle within the detected ovary further comprises:
defining a seed point for each candidate follicle in the plurality of 2-D ultrasound images, and for each seed point, applying an adaptive region growing algorithm to the plurality of 2-D ultrasound images to segment the candidate follicle associated with said seed point.

5. The computer-implemented method of claim 4, further comprising:
receiving a user-defined additional seed point and applying the adaptive region growing algorithm to the plurality of 2-D ultrasound images to segment the candidate follicle associated with said user-defined additional seed point; and/or
receiving a user-identified existing seed point and deleting the user-identified existing seed point from the defined seed points.

6. The computer-implemented method of claim 4, further comprising:
determining a form factor of a pixel area obtained with the adaptive region growing algorithm; and
rejecting the candidate follicle if said form factor is below a defined form factor threshold.

7. The computer-implemented method of claim 3, further comprising:
determining an area of overlap between overlapping segmented candidate follicles; and
deleting the overlapping segmented candidate follicle having the smaller average diameter if said area of overlap exceeds a defined overlap threshold.

8. The computer-implemented method of claim 1, wherein determining an average diameter for each candidate follicle comprises:

determining an average diameter of a follicle portion in each 2-D ultrasound image comprising a portion of the follicle;
selecting the 2-D ultrasound image having the largest average diameter of the follicle portion; and
selecting said largest average diameter as the average diameter of the follicle.

9. A computer program product comprising a non-transitory computer readable storage medium having computer readable program instructions embodied therewith for, when executed on a processor arrangement of an ultrasound image processing device, cause said processor arrangement to implement a method comprising:
receiving a pair of 2-D (two-dimensional) transvaginal ultrasound scans, each scan comprising a plurality of 2-D ultrasound images captured along a translation direction of an ultrasound probe used to capture said scan, the respective translation directions being at least approximately orthogonal, and for each of said scans, the method further comprising:
determining at least one of ovarian rotation and truncation in a detected ovary of each of the 2-D (two-dimensional) transvaginal ultrasound scans;
detecting candidate follicles in the plurality of 2-D ultrasound images of the 2-D transvaginal ultrasound scan wherein detecting candidate follicles in the plurality of 2-D ultrasound images comprises:
approximating a volume image from the plurality of 2-D ultrasound images;
detecting the ovary in the approximated volume image;
detecting possible candidate follicles within the detected ovary;
determining a volume for each candidate follicle; and
rejecting the candidate follicles that have a determined volume below a defined volume threshold for subsequent segmenting;
segmenting the detected candidate follicles to determine an average diameter for each candidate follicle;
selecting the 2-D transvaginal ultrasound scan including the candidate follicle having the largest average diameter;
presenting the determined average diameters and the segmentations of the detected candidate follicles of the selected 2-D transvaginal ultrasound scan.

10. An ultrasound image processing device comprising a processor arrangement adapted to implement a method comprising:
receiving a pair of 2-D (two-dimensional) transvaginal ultrasound scans, each scan comprising a plurality of 2-D ultrasound images captured along a translation direction of an ultrasound probe used to capture said scan, the respective translation directions being at least approximately orthogonal, and for each of said scans, the method further comprising:
determining at least one of ovarian rotation and truncation in a detected ovary of each of the 2-D (two-dimensional) transvaginal ultrasound scans;
detecting candidate follicles in the plurality of 2-D ultrasound images of the 2-D transvaginal ultrasound scan, wherein detecting candidate follicles in the plurality of 2-D ultrasound images comprises:
approximating a volume image from the plurality of 2-D ultrasound images;
detecting the ovary in the approximated volume image;
detecting possible candidate follicles within the detected ovary;
determining a volume for each candidate follicle; and rejecting the candidate follicles that have a determined volume below a defined volume threshold for subsequent segmenting;

segmenting the detected candidate follicles to determine an average diameter for each candidate follicle;

selecting the 2-D transvaginal ultrasound scan including the candidate follicle having the largest average diameter; and presenting the determined average diameters and the segmentations of the detected candidate follicles of the selected 2-D transvaginal ultrasound scan wherein:

the ultrasound image processing device further comprises a computer program product of the processor arrangement being adapted to execute computer readable program instructions embodied by said computer program product.

11. An ultrasound imaging system comprising:

an ultrasound image processing device comprising: a processor arrangement adapted to implement a method comprising:

receiving a pair of 2-D (two-dimensional) transvaginal ultrasound scans, each scan comprising a plurality of 2-D ultrasound images captured along a translation direction of an ultrasound probe used to capture said scan, the respective translation directions being at least approximately orthogonal, and for each of said scans, the method further comprising:

determining at least one of ovarian rotation and truncation in a detected ovary of each of the 2-D (two-dimensional) transvaginal ultrasound scans;

detecting candidate follicles in the plurality of 2-D ultrasound images of the 2-D transvaginal ultrasound scan, wherein detecting candidate follicles in the plurality of 2-D ultrasound images comprises:

approximating a volume image from the plurality of 2-D ultrasound images;

detecting the ovary in the approximated volume image;

detecting possible candidate follicles within the detected ovary;

determining a volume for each candidate follicle; and rejecting the candidate follicles that have a determined volume below a defined volume threshold for subsequent segmenting;

segmenting the detected candidate follicles to determine an average diameter for each candidate follicle;

selecting the 2-D transvaginal ultrasound scan including the candidate follicle having the largest average diameter; and presenting the determined average diameters and the segmentations of the detected candidate follicles of the selected 2-D transvaginal ultrasound scan; and an ultrasound probe for providing the ultrasound image processing device with said pair of transvaginal ultrasound scans.

* * * * *